(12) United States Patent
Mahnke et al.

(10) Patent No.: US 11,754,513 B2
(45) Date of Patent: Sep. 12, 2023

(54) ABSORPTION IMAGING APPARATUS AND DETECTOR ARRAY THEREFOR

(71) Applicant: Mettler-Toledo, LLC, Columbus, OH (US)

(72) Inventors: Guido Mahnke, Wiesbaden (DE); Benedikt Hoffmann, Idstein (DE)

(73) Assignee: Mettler-Toledo, LLC, Columbus, OH (US)

( * ) Notice: Subject to any disclaimer, the term of this patent is extended or adjusted under 35 U.S.C. 154(b) by 128 days.

(21) Appl. No.: 17/444,322

(22) Filed: Aug. 3, 2021

(65) Prior Publication Data
US 2022/0042927 A1 Feb. 10, 2022

(30) Foreign Application Priority Data

Aug. 4, 2020 (EP) ..................... 20189361

(51) Int. Cl.
*G01N 23/04* (2018.01)
*G01N 23/083* (2018.01)
*G01N 23/10* (2018.01)

(52) U.S. Cl.
CPC .......... *G01N 23/04* (2013.01); *G01N 23/083* (2013.01); *G01N 23/10* (2013.01); *G01N 2223/501* (2013.01)

(58) Field of Classification Search
CPC ...... G01N 23/04; G01N 23/10; G01N 23/083; G01N 23/087; G01N 2223/501; G01N 33/02; G01T 1/20182; G01T 1/243; G01T 1/2985; G01V 5/0041; G01V 5/005
See application file for complete search history.

(56) References Cited

U.S. PATENT DOCUMENTS

| | | | |
|---|---|---|---|
| 4,511,799 A | 4/1985 | Bjorkholm | |
| 6,760,404 B2 | 7/2004 | Saito et al. | |
| 7,162,007 B2 | 1/2007 | Elyan et al. | |
| 9,915,751 B2 | 3/2018 | Kang et al. | |
| 9,945,714 B1 | 4/2018 | Hartwig | |
| 10,371,854 B2 | 8/2019 | Zhao et al. | |
| 2009/0285353 A1* | 11/2009 | Ellenbogen | ............ G01V 5/005 378/57 |

FOREIGN PATENT DOCUMENTS

EP 1010021 B1 10/2004

* cited by examiner

*Primary Examiner* — Jurie Yun
(74) *Attorney, Agent, or Firm* — STANDLEY LAW GROUP LLP; Jeffrey S. Standley; Adam J. Smith (57) ABSTRACT

An array (1) for detecting electromagnetic radiation is provided for a radiographic inspection system (20). The array has a plurality of detector elements (2) arranged consecutively along a scan line which extends in a first direction (Y). Each of the detector elements has a detection surface (3) for receiving electromagnetic radiation and converting the received electromagnetic radiation into a corresponding detection signal. Each detection surface (3) has a surface normal (4, N) that extends in a common plane (S) and converges into a common focus (5). The common plane (S) extends in the first direction (Y). The distances between the common focus and the detection surfaces along the respective surface normal (4, N) are different for at least two detector elements.

16 Claims, 6 Drawing Sheets

FIG. 1

$$\frac{a}{a'} = \frac{b}{b'}$$

ABSORPTION IMAGING APPARATUS AND DETECTOR ARRAY THEREFOR

CROSS-REFERENCE TO RELATED APPLICATIONS

This application is a non-provisional application that makes a claim of priority to European patent application 20189361.7, filed on 4 Aug. 2020, which is incorporated by reference as if fully recited herein.

TECHNICAL FIELD

The disclosed invention relates to an array for detecting electromagnetic radiation. The detector array comprises a plurality of detector elements arranged consecutively along a scan line which extends in a first direction. Each of the detector elements has a detection surface that receives electromagnetic radiation and converts the received electromagnetic radiation into a corresponding detection signal. Normals to each of the detection surfaces extend in a common plane and converge into a common focus. Furthermore, A radiographic inspection system is also disclosed that has the disclosed detector array.

BACKGROUND

A detector array for radiographic inspection may comprise a detector having a plurality of detector elements arranged in a two-dimensional arrangement, e. g. an m×n matrix, as it is disclosed e. g. in US 2002/0110216 A1. Alternatively, a plurality of detector arrays having a scan line that extends in a first direction may be arranged in a direction perpendicular to the first direction to create a two-dimensional arrangement, as it is disclosed e. g. in EP 1 010 021 B1. The detector elements comprise a detection surface for receiving electromagnetic radiation and are operative to convert the received electromagnetic radiation into a corresponding detection signal. The radiation surfaces may comprise a scintillator adapted to convert the electromagnetic radiation into radiation detectable by a photodiode. A photodiode may be arranged on each of the detector elements.

A radiographic inspection system may comprise a detector array, a radiation source for producing a radiation beam comprising a bundle of rays, said rays spanning a radiation plane and transport means for transporting an article to be inspected along a transport path transverse to said radiation plane, said transport path being interposed between the radiation source and the detector array. The radiation source may be an X-ray source.

For example, in a known setup of a radiographic inspection system, as it is described in EP 3 078 944 A1, an article to be inspected is transported on a conveyor belt along a transport path interposed between a radiation source and a detector array. Typically, the electromagnetic radiation of the radiation source is emitted as a fan-shaped planar bundle of rays. The detector has the form of a linear array of detector elements arranged along a scan line which extends in a first direction. The radiation plane spanned by the fan-shaped radiation beam and the detector array lie in a plane which runs substantially perpendicularly to the transport path of the article. While the article moves through the plane, the update frequency of the detector is coordinated with the speed of the conveyor belt, so that the sequence of signals generated by the detector array can be translated into a pattern of raster dots with different brightness values representing a shadow image of the article interposed between the radiation source and the radiation detector. The shadow image corresponds to a transmission image of the article, i.e. it corresponds to the X-rays transmitted through and absorbed by the article. The absorption is then determined from the transmission image. In this way, a two-dimensional image of the article to be inspected may be generated. If a scanned article contains foreign objects such as metal fragments, which have a lower transmittance to the rays of the radiation source than the scanned article, the radiographic image will show such foreign objects as darker areas within the transparent shadow image of the scanned article.

Radiographic inspection has many applications, including, but not limited to, the food and beverage industry where it is used to detect foreign material in an article, or forensic science. For example, the radiographic inspection system explained above may be used to detect foreign objects in food, for example in meat.

In many applications, absorption imaging using X-rays is used for imaging an article comprising a plurality of materials of unknown thickness. In this case it is beneficial to record not just one X-ray absorption image, but to record multiple images of the same object at different X-ray energies. From these images it is then possible to distinguish between different materials based on their energy-dependent X-ray absorption.

The most common method to record multiple images of the same article at different X-ray energies is dual energy X-ray imaging. There, the same article is either exposed to varying X-ray energies, or a detector capable of resolving two or more different energies is used.

There are various technical realizations of detectors capable of resolving two or more different energies. In general, such a detector consists of multiple detector elements capable of recording X-ray signals independently of each other. Modern semiconductor detectors can measure the energy of individual X-ray photons (photon counting) and may therefore resolve the X-ray photon energy in every detector element.

Another possibility for a dual energy X-ray detector uses a scintillator for converting X-ray photons into visible light and photodiodes for detecting the emitted light. Commonly, detector elements comprising first and second detector members having scintillators with different scintillator materials and thicknesses are used to form a dual energy X-ray detector.

The first and second detector members of each detector element may be placed side by side. Alternatively, the first and second detector members may be stacked, as it is disclosed in U.S. Pat. No. 4,511,799. For a stacked-type dual-energy X-ray detector, the first ("upper") detector member facing the X-ray source generally records the low energy image. Below the upper detector member, a filter, for example a thin metal plate, may be arranged to block low energy X-rays from reaching the second ("lower") detector member arranged underneath and adapted to record a high energy image.

As it was explained above and is further explained with reference to FIG. 5 which shows a schematic sectional view of a radiographic inspection system, a radiographic inspection system used for imaging a moving article may comprise a detector array 100 comprising a plurality of detector elements 101 arranged consecutively along a scan line extending in a first direction Y and a radiation source 120 emitting a radiation beam comprising a bundle of rays 132, said rays 132 spanning a radiation plane. The detector elements 100 comprise detection surfaces for receiving electromagnetic radiation and being operative to convert the received electromagnetic radiation into a corresponding detection signal. The detection surfaces are arranged perpendicularly to the radiation plane. The detector array 100 may be arranged symmetrically with respect to the focal spot 131 of the radiation beam 130. Thus, the radiation incident on the detection surfaces 101 of the detector array 100 may have an angle of incidence a of approximately 90° at the center C of the detector array 100. Towards the outer ends of the detector array 100, the angle of incidence a is, however, different from 90°.

Figure 5:
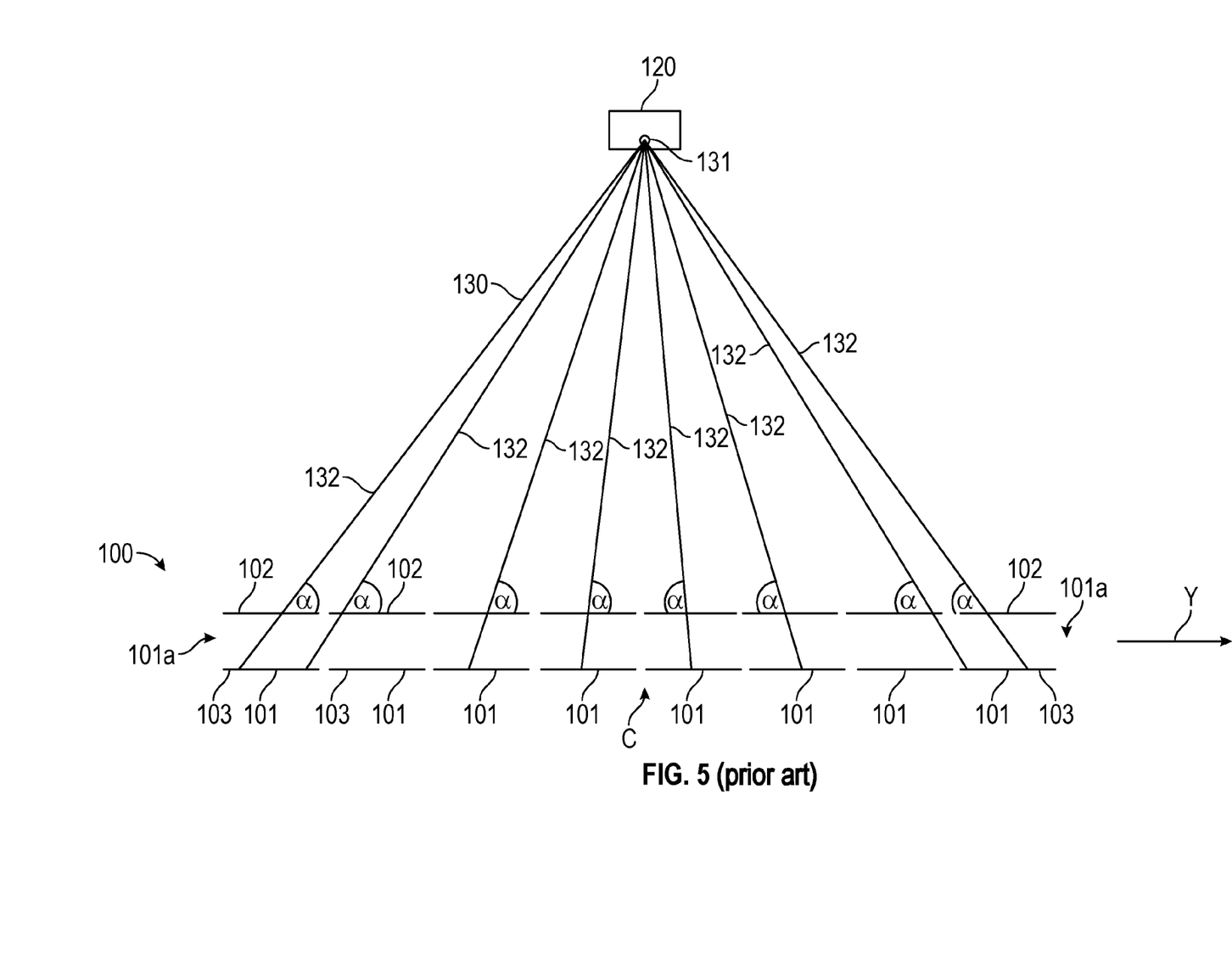
FIG. 5 is a side view of a detector array and a radiation source according to the state of the art.

In the case of a detector array 100 comprising stacked-type dual-energy X-ray detector elements 101, each comprising an upper detector member 102 and a lower detector member 103 wherein each of the detector members 102, 103 has a detection surface, as it is depicted in FIG. 5, an angle of incidence a on the detection surfaces of the upper and lower detection members 102, 103 different from 90° may have the following consequences: At the edges 101*a* of the flat detector array 100, a ray 132 incident on the detector array 100 may be incident on the upper detector member 102 of one detector element 101, but the ray 132 is not incident on the lower detector member 103 of the same detector element 101. Instead, the ray 132 is incident on the lower detector member 103 of a neighboring detector element 101. This deteriorates the resolution of the detector array 100.

Figure 6:
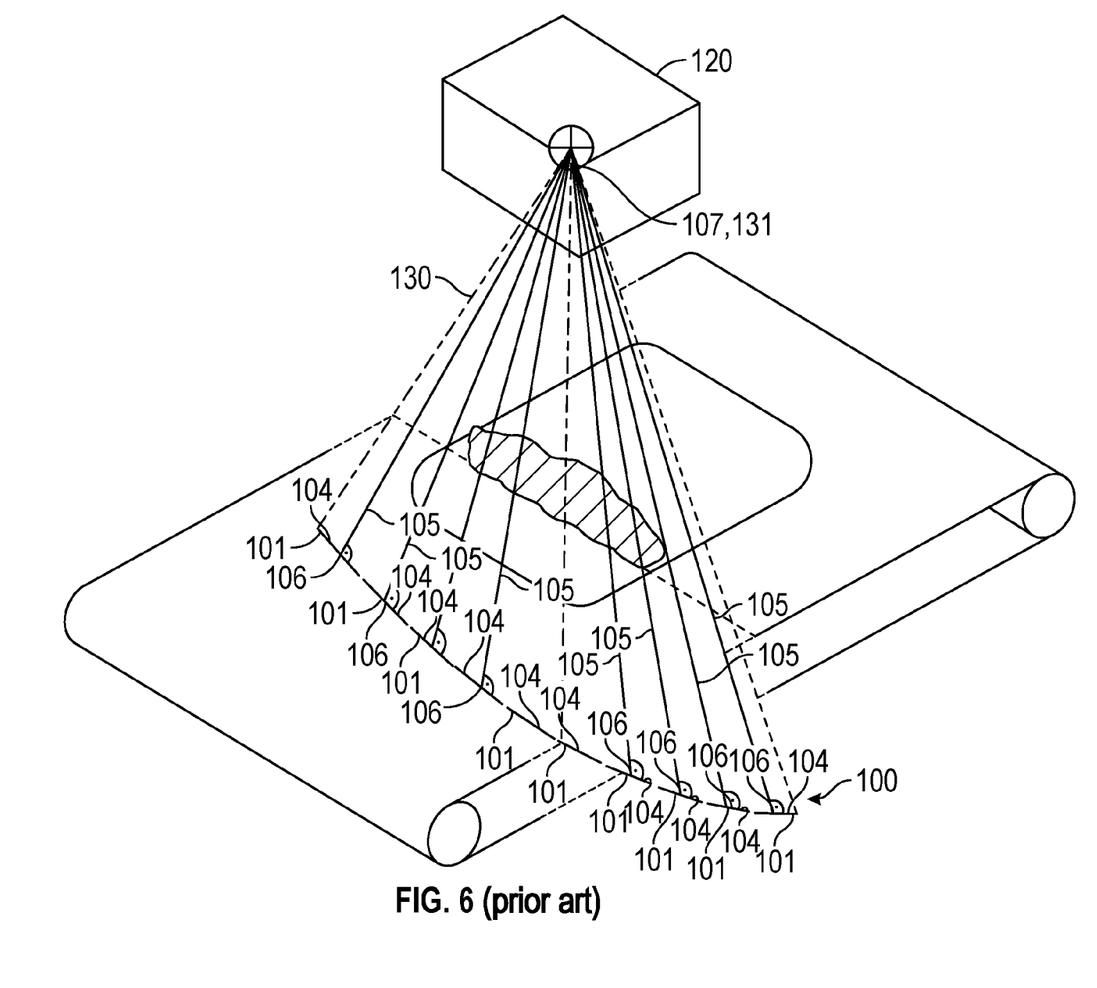
FIG. 6 is a perspective view of a radiographic inspection system according to the state of the art.

To improve this situation, it is known in the art to arrange the detector elements 101 of a detector array 100 consecutively on an arc (see FIG. 6). Each detector element 101 has a detection surface 104 for receiving electromagnetic radiation, wherein surface normals 105 of each of said detection surfaces 104 extend in a common plane and converge into a common focus 107. When the detector array 100 and the radiation source 120 are arranged with respect to each other such that the common plane coincides with a radiation plane spanned by the rays 132 of a radiation beam 130 emitted from the radiation source 120 and said common focus 107 coincides with the focal spot 131 of the radiation beam 130, each detector element 100 is illuminated by the radiation beam 130 under an angle of 90° at its centroid 106.

Current developments in X-ray imaging technology have led to a decreasing size of the pixels in X-ray detectors. This development is in response to the need for better image quality, for example to detect smaller contaminants in food inspection. This development brings along additional challenges for building X-ray detectors. While the arc arrangement of the individual detector elements mentioned above implies that electromagnetic radiation is incident on the upper and lower detector members of a stacked-type dual-energy X-ray detector element at the centroid of each detection surface at an angle of approximately 90°, this is no longer true towards the edge of an individual detector element. There, an incident angle deviating from 90° will occur. Thus, as in the case of a flat detector array, a ray incident on the upper detector member of a detector element may not be incident on the lower detector member of the same detector element. This effect may be relevant for a detector element of a size of 0.4 mm as it is available today. Thus, the resolution gain of the small detector element may be lost.

Another challenge for detector arrays known in the art is the precise alignment of the detector elements along the first direction. When all detector elements are aligned on an arc, a gap between two neighboring detector elements should be kept as small as possible since no radiation is detectable in the gap. This requires a careful alignment of the detector elements and poses the risk of damaging the edges of the detector elements during mounting. Alternatively, there may be relatively large gaps between the neighboring detector elements which decrease the resolution of the detector array.

In view of the problems in the prior art, it is therefore an object of the present invention to further develop a detector array and a radiographic inspection system mentioned above so that a high precision detection and a simple production is achieved.

SUMMARY

According to a first aspect of the present invention, this object is attained by further developing the detector array mentioned above in that the common plane extends in said first direction and the distances between the common focus and the detection surfaces along the normal direction are different for at least two detector elements.

According to the first aspect of the present invention, there is provided a detector array for detecting electromagnetic radiation, said detector array comprising a plurality of detector elements. The plurality of detector elements may comprise two, three or more detector elements. The detector elements are arranged consecutively along a scan line which extends in a first direction. This arrangement realizes a "one-dimensional" detector array. During use of the detector array, an article to be inspected is moved along a transport path transverse, e. g. perpendicular, to the scan line to create a two-dimensional image. Several detector arrays according to the present invention may be arranged along the direction transverse, e. g. perpendicular, to the scan line.

Each of said detector elements has a detection surface for receiving electromagnetic radiation and being operative to convert the received electromagnetic radiation into a corresponding detection signal. The detection signal may be an electric signal. Each of the detection surfaces comprises a plurality of surface normals. For each of the detection surfaces there exists at least one surface normal such that the surface normals extend in a common plane, and said common plane extends in said first direction. That is, all these surface normals lie within the common plane. A direction along a surface normal is denoted as a normal direction. Furthermore, the surface normals all converge into a common focus. The common focus may be a point or a region. For example, when the detection elements are arranged on an arc with center point M, as it is known in the prior art (see FIG. 6), the common focus corresponds to the center M, and the surface normals are normal to the centroids of the detection surfaces of the individual detector elements.

According to the first aspect of the present invention, the distances between the common focus and the detection surfaces along the normal direction are different for at least two detector elements. I. e., if one defines a distance d1 as the distance between the detection surface of one of the two detector elements and the common focus along the surface normal of the one detector element converging in the common focus, and if one defines a distance d2 between the detection surface of the other one of the two detector elements and the common focus along the surface normal of the other one of the two detector elements converging in the common focus, then d1 is different from d2. That is, at least two detector elements are offset from each other in the common plane. This is different from the arrangement where all detector elements are arranged on an arc. When arranged on an arc, the distances between the common focus and the detection surfaces along the normal directions are the same for all detector elements.

The offset of at least two of the detector elements simplifies the alignment between neighboring detector boards, allows for an easy mounting of a large number of small detector elements and reduces the volume of the detector array as the height of the detector array may be reduced. The height of the detector array may be defined as the maximum extension of the detector array in the common plane.

In one embodiment of the detector array according to the present invention, facing end surfaces of at least two neighboring detector elements may be aligned along a straight line through the common focus. The facing end surfaces are facing each other in the first direction. In this embodiment, there is no region between the two neighboring detector elements where radiation emitted in a radiation beam, e. g. a fan-shaped radiation beam, from a radiation source located in the common focus of the detector array is not detectable by the detector array. I. e., there are no gaps between neighboring detector elements in the first direction where radiation is not detectable. Thereby, the detection efficiency of the detector array is improved. In one possible example, facing end surfaces of every pair of neighboring detector elements may be aligned along a straight line through the common focus. In this way, the detection efficiency may be further improved.

According to another embodiment of the detector array according to the present invention, there may be, for each of the detector elements, at least one neighboring detector element such that the distances between the common focus and the detection surfaces along the normal direction are different for the two neighboring detector elements. This arrangement allows to minimize the extension of the detector array in the normal direction. I. e., the height of the detector array may be reduced.

In another embodiment of the detector array according to the present invention, there may be, for each of said detection surfaces, a surface normal at a centroid of the respective detection surface converging in said common focus. In this way, the angle of incidence of radiation at the centroid of each of the detection surfaces in the first direction is 90°. However, the invention is not limited to this configuration. For example, for each of said detection surfaces there may be a surface normal at an end portion of the detection surface in the first direction, said surface normals converging in a common focus. When a radiation source is arranged in the common focus of the detector array, the angle of incidence of radiation at the end portion of each of the detection surfaces in the first direction is then 90°.

Furthermore, said centroids of said detection surfaces may be aligned along a straight line. The straight line may extend in the first direction. In this way, the height of the detector array may be limited by the size of the detection surfaces. Thus, the height of the detector array may be further reduced.

In one embodiment of the detector array according to the present invention, a more constant magnification factor in the resulting image may be achieved by setting for at least one pair of detector elements the distances a and b between two points A and B, each of which being located at an intersection of a surface normal at a centroid of a detection surface of the respective detector element of the pair of detector elements and a detection plane for arranging an article to be inspected, and the common focus and the distances a' and b' between said points A and B and the respective detection surface to a constant distance ratio $a/a'=b/b'$. In use of the detector array, an article to be inspected is arranged in a detection plane. Then, one may identify for at least one pair of first and second detector elements a point A at an intersection of the surface normal at the centroid of the detection surface of the first detector element and the detection plane. Furthermore, one may identify a point B at an intersection of the surface normal at the centroid of the detection surface of the second detector element and the detection plane. Then, the distance between the common focus and the point A is denoted by a and the distance between the point B and the common focus is denoted by b. Furthermore, the distance between the point A and its projection onto the first detector element is denoted by a' and the distance between the point B and its projection onto the second detector element is denoted by b'. Since the detector elements are arranged in the detector array such that the distance ratio $a/a'=b/b'$ is the same for the at least two detector elements, a more constant magnification factor may be guaranteed. I.e., a region of size s of an article in the vicinity of the point A and a region of size s of an article in the vicinity of the point B are enlarged to an image of approximately the same size at the detector array. In this way, a problem of state of the art detector arrays is overcome, where the magnification factor is not constant over the whole detector array. Preferably, the distance ratio $a/a'=b/b'$ is the same for each pair of detector elements of the detector array.

There are various possible geometries for the detection surfaces of the detector elements. For example, at least one of the detection surfaces may comprise a flat surface. Such detection surfaces are especially easy to produce. Additionally or alternatively, said detection surfaces may have a rectangular circumference. Then, the centroid corresponds to the center of the rectangle. This is beneficial for arranging the detector elements consecutively along the first direction.

The detector array mentioned above may be used to detect electromagnetic radiation of arbitrary wavelength. In one possible embodiment of the detector array according to the present invention, the detector elements may be adapted to detect X-ray radiation. Then, the detector according to the present invention may be used, for example, for X-ray absorption imaging.

In one embodiment of the present invention, the detector elements may comprise a stacked-type dual-energy X-ray detector element. A stacked-type dual-energy X-ray detector element comprises a first detector member and a second detector member stacked on top of each other. The first and second detector members comprise first and second detection surfaces, respectively. The first and second detection surfaces are operative to convert the received electromagnetic radiation into a corresponding detection signal. The first and second detection surfaces comprise surface normals wherein for each surface normal on the first detection surface there may exist a surface normal on the second detection surface such that the surface normals are aligned along one straight line. The first and second detection surfaces may comprise flat surfaces arranged parallel to each other. The first ("upper") detector member which will face the radiation source during use of the detector array is adapted to detect a first radiation energy E1. The second ("lower") detector member arranged below the upper detector member is adapted to detect electromagnetic radiation with a second energy E2. The first and the second detector members may be adapted such that the upper detector member detects an energy lower than the lower detector member, i. e. E1<E2. Between the upper and the lower detector members, a filter, for example a thin metal plate, may be arranged to prevent low energy radiation from reaching the lower detector member.

In one embodiment of the detector array according to the present invention, each of said detector elements may comprise a scintillator. The scintillator may be adapted to convert the electromagnetic radiation into radiation detectable by a photodiode. Each detector element may comprise a photodiode adapted to detect the radiation emitted from the scintillator.

In another example of the detector array according to the present invention, the detector array may further comprise a support, and each detector element may be detachably mounted on said support. This allows for a very easy replacement of damaged detector elements. For example, each detector element may comprise a protrusion, and the support may comprise a plurality of recesses adapted to receive said protrusions such that the detector elements are stably mountable on said support.

According to a second aspect of the present invention, there is provided a radiographic inspection system, the system comprising: a radiation source for producing a radiation beam comprising a bundle of rays, said rays spanning a radiation plane, the radiation beam comprising a focal spot; a detector array according to the present invention; transport means for transporting an article to be inspected along a transport path transverse to said radiation plane, said transport path being interposed between said radiation source and said detector array, wherein said detector array is arranged such that said common plane coincides with said radiation plane and said common focus coincides with said focal spot.

According to an embodiment of the present invention, said transport means may comprise a conveyor belt. The transport path may be perpendicular to said radiation plane.

According to another aspect of the present invention, said radiation source may comprise an X-ray source. The radiographic inspection system may be a system for absorption imaging, in particular for X-ray absorption imaging. The radiation source may emit a fan-shaped radiation beam, the rays of said beam spanning the radiation plane.

BRIEF DESCRIPTION OF THE DRAWINGS

In the following description, the invention will be specified in greater detail by way of example with reference to the drawings. In the drawings.

DETAILED DESCRIPTION

Figure 1:
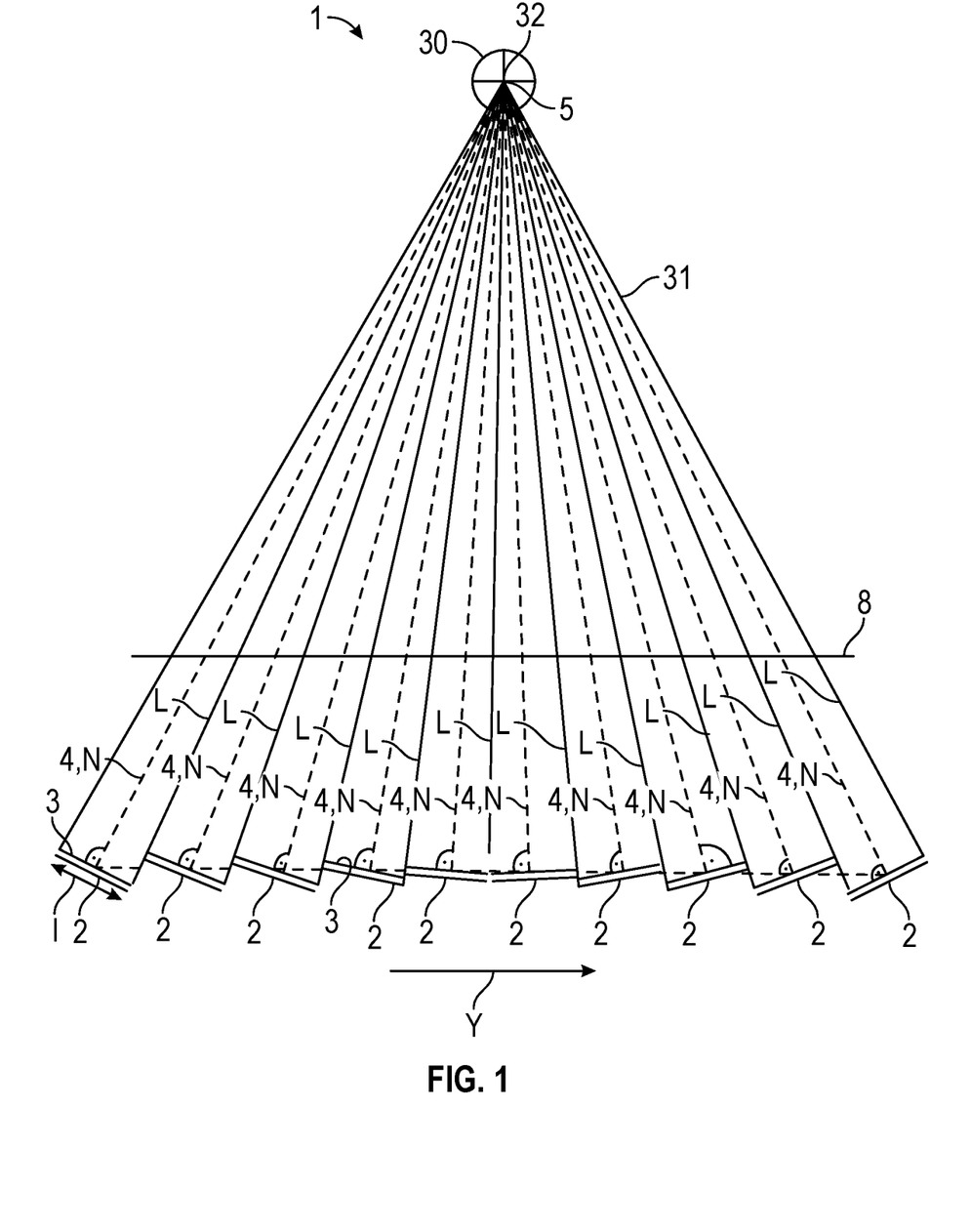
FIG. 1 is a side view of a detector array according to the present invention, wherein a common focus of the detector array is arranged in the focal spot of a radiation source.

FIG. 1 is a side view of a detector array 1 according to the present invention. The detector array 1 comprises a plurality of detector elements 2 arranged consecutively along a scan line which extends in a first direction Y.

FIG. 1 further shows a radiation source 30 emitting electromagnetic radiation comprising a bundle of rays. In FIG. 1, the beam is in the form of a fan-shaped radiation beam 31, but the invention is not limited to this. The rays of the radiation beam span a radiation plane RP. In FIG. 1, the radiation plane RP coincides with the paper plane.

An article to be inspected may be transported through the radiation plane RP. To this end, a belt conveyor may be used. The belt conveyor may transport the article in an inspection plane 8 transverse, in particular perpendicular, to said radiation plane RP.

Each of said detector elements 2 has a detection surface 3 for receiving electromagnetic radiation and operative to convert the received electromagnetic radiation into a corresponding detection signal. Surface normals 4 of each of the detection surfaces 3 extend in a common plane S, said common plane S extending in said first direction Y. The surface normals 4 converge into a common focus 5. I. e., the surface normals 4 all lie within the common plane S. Each surface normal 4 defines a normal direction N. Unlike in an arc-shaped arrangement of the detection elements as it is known in the art, there is for each detector element 2 a neighboring detector element 2 such that the distances between the common focus 5 and detection surfaces 3 along the normal direction N are different for the two neighboring detector elements 2. I. e., if one defines as d1 the distance between a detection surface 3 of one of the two detector elements 2 and the common focus 5 along the surface normal N of the one detector element 2 converging in the common focus 5, and if one defines as d2 the distance between the detection surface 3 of the other one of the two neighboring detector elements 2 and the common focus 5 along the surface normal N of the other detector element 2 converging in the common focus, then d1 is different from d2. As it is immediately clear from FIG. 1, the height of the detector array 1, i. e. the extension of the detector array 1 in the common plane S, is limited by the length 1 of the detection surfaces 3 shown in FIG. 1. In this way a very compact arrangement of the detector elements, and thus a very compact detector array 1, can be realized. Furthermore, the detector array 1 allows for an easy mounting and/or replacement of individual detector elements 2.

Figure 2:
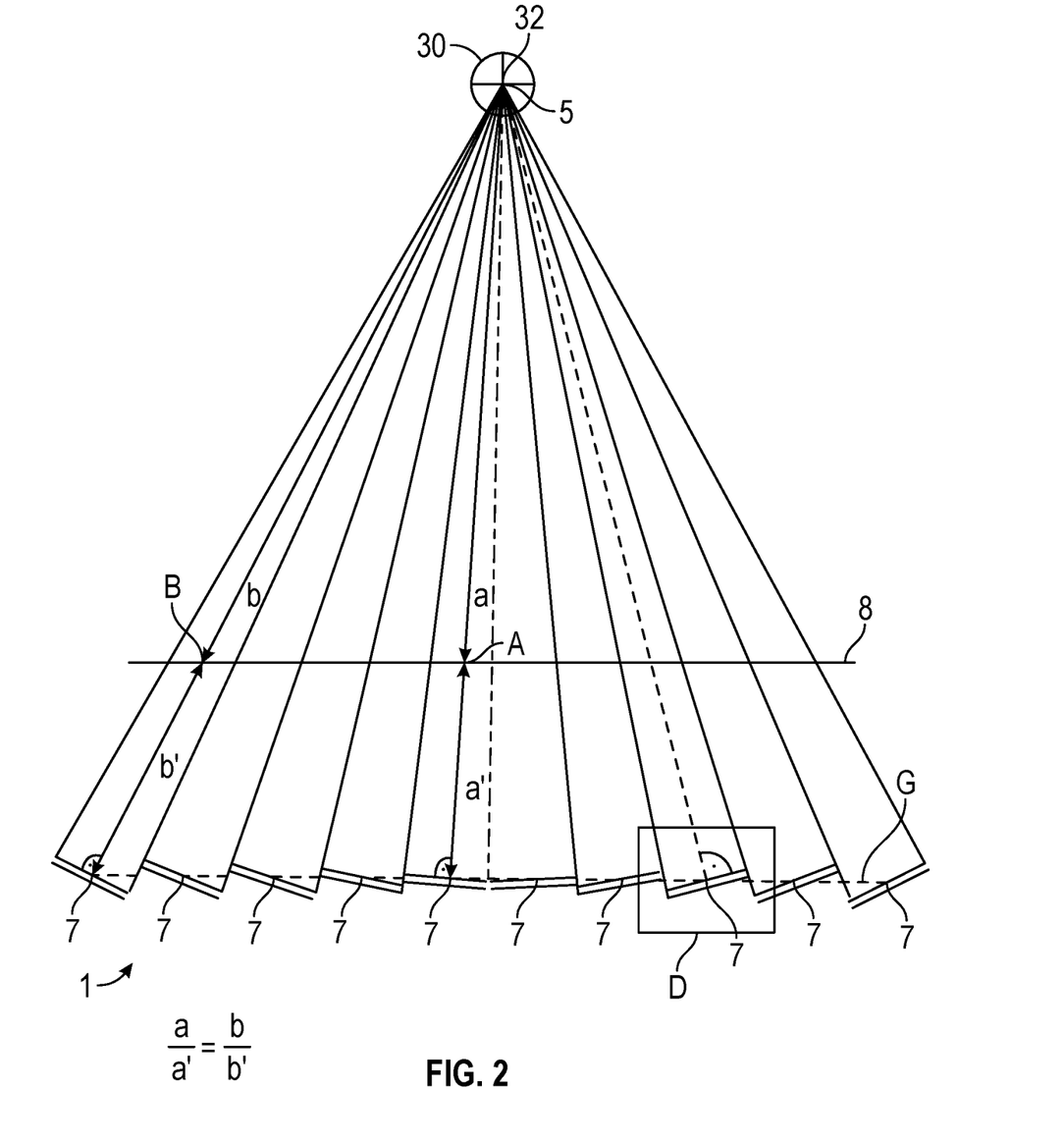
FIG. 2 is a similar view to the one shown in FIG. 1, which illustrates geometrical relationships of the detector array.
Figure 3:
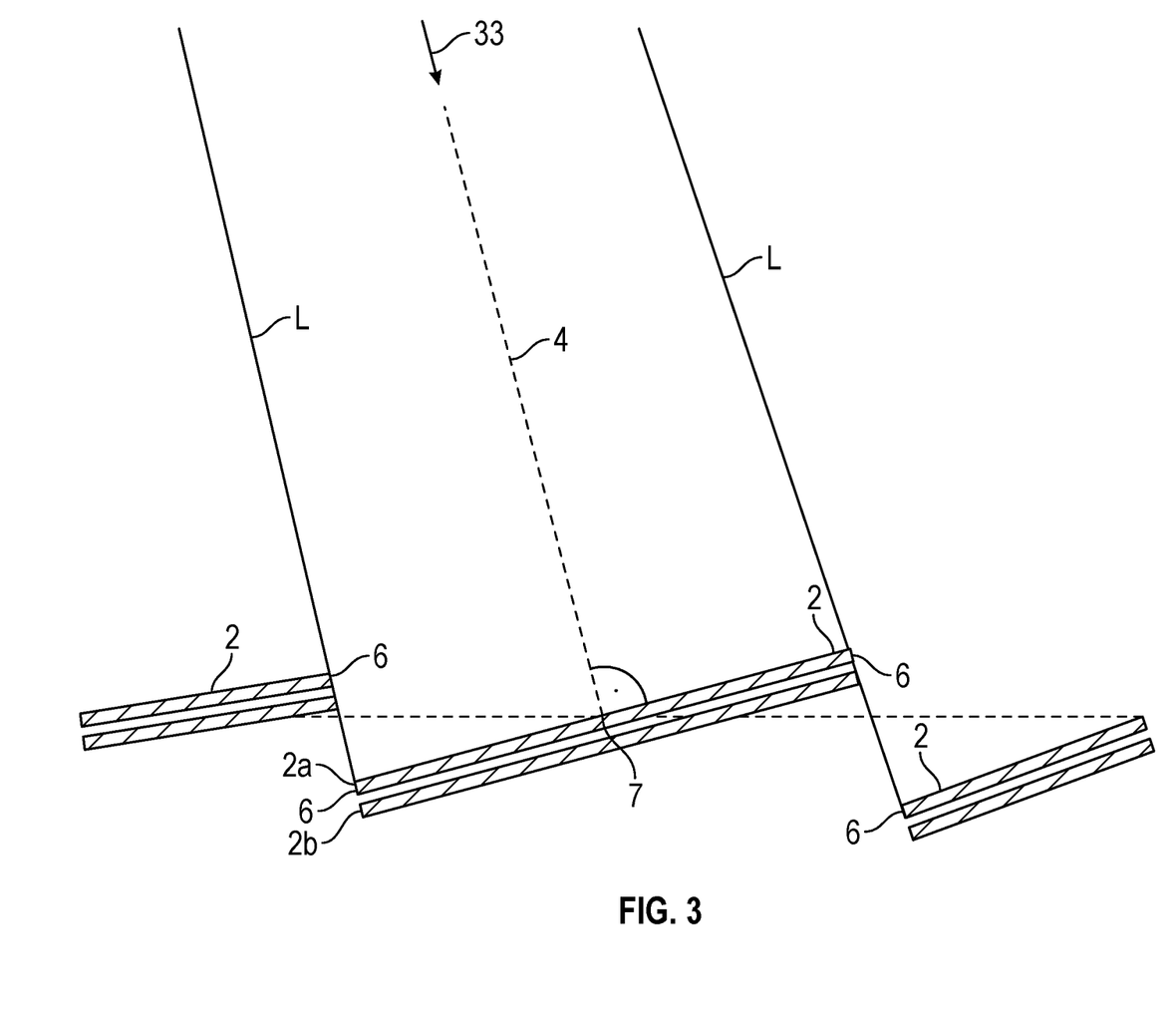
FIG. 3 is an enlarged view of region D in FIG. 2.

Furthermore, as can be seen best in FIG. 3, which is an enlarged view of the region D of the embodiment shown in FIGS. 1 and 2, facing end surfaces 6 of neighboring detector elements 2 are aligned along a straight line L through the common focus 5. In this way, there is no gap between neighboring detector elements 2 in the first direction Y where radiation of the fan-shaped beam 31 is not detectable. This improves the detection efficiency of the detector array 1 compared to arrangements where there is a gap between the neighboring detector elements such that radiation is not received from either of the two neighboring detector elements 2.

Furthermore, in the embodiment shown in FIG. 1, there exists for each of said detection surfaces 3 a surface normal 4 at a centroid 7 of the respective detection surfaces 3, wherein said surface normal 4 converges in the common focus 5 (see the enlarged view of FIG. 3). The detection surfaces 3 may have a rectangular circumference and may be flat. Then, the centroid 7 corresponds to the center of the flat, rectangular detection surface. I. e., in the case shown in FIG. 1 where a focal spot 32 of the radiation source 30 coincides with the common focus 5 of the detector array 1, the radiation emitted in the fan-shaped radiation beam 31 is incident on the detection surfaces 3 of the detector elements 2 in the centroid 7 of the detection surfaces 3 at an angle of 90° (see FIG. 3).

Each of the detector elements 2 of the embodiment shown in FIG. 1 may comprise a stacked-type dual-energy X-ray detector element. This will be explained in more detail with reference to FIG. 3 below.

As mentioned above, the detector elements 2 may comprise detection surfaces 3 having a flat surface. Furthermore, said detection surfaces 3 may have a rectangular circumference. In this way, it may be particularly easy to arrange the detector elements 2 in the detector array 1.

In absorption imaging, a region of a size s of an article to be inspected is represented as an image on the detector array, wherein the size s' of the image of the region is larger than the size s of the region of the article. This effect is called magnification, and s'/s is called the magnification factor. A problem of state of the art detector arrays is a non-constant magnification factor. I.e., two regions of the same size of the article to be inspected are represented as images of different size at the detector. This problem may be overcome by the detector array of the present invention. To this end, it is referred to FIG. 2 which is a similar view to the one shown in FIG. 1, which illustrates geometrical relationships of the detector array 1. Let A and B denote two points, each of which being located at an intersection of a surface normal 4 at a centroid 7 of a detection surface 3 of first and second detector elements 2 and the inspection plane 8. The distance between the common focus 5 and the point A will be denoted as a, the distance between the common focus 5 and the point B will be denoted as b, the distance between the point A and the first detector element of the detector array 1 along the surface normal 4 will be denoted as a', and the distance between the point B and the second detector element of the detector array 1 along the surface normal 4 will be denoted as b'. Then, as all centroids 7 of the detector elements 2 are arranged on a single straight line G, it follows from the intercept theorem that the distance a/a'=b/b' is constant. Due to this relationship, a more constant magnification factor can be guaranteed. I. e., a region of size s of an article in the vicinity of point A and a region of size s of an article in the vicinity of point B on a conveyor belt in the inspection plane 8 will be enlarged to an image of (approximately) the same size at the respective detector elements 2 of the detector array 1. Preferably, the distance ratio defined above is the same for each pair of detector elements 2.

FIG. 3 is an enlarged view of the region D in FIG. 2. FIG. 2 depicts a detector element 2 comprising a stacked-type dual-energy X-ray detector element. Each of the detector elements 2 comprises a first detector member 2a and a second detector member 2b stacked on top of each other. The first detector member 2a faces the radiation source 30. The first detector member 2a may be adapted to detect radiation at an energy E1, and the second detector member 2b may be adapted to detect radiation at an energy E2, wherein E2 is bigger than E1. I. e., the first detector member 2a may be considered as a low-energy detector, and the second detector member 2b may be considered as a high-energy detector. As the first and second detector members 2a, 2b are stacked on top of each other, a ray 33 of the radiation beam 31 is incident at a centroid 7 of the detection surfaces 3 of the first and second detector members 2a, 2b at an angle of 90°. There may be a distance between the first and second detector members 2a, 2b. Thus, the problem of the prior art where a ray incident on an upper detector member of a detector element is not incident on a lower detector member of the same detector element but on a neighboring detector element is prevented with a detection array according to the present invention. In this way, the resolution of the detector array 1 is improved compared to arrangements in the state of the art where the detection surfaces are arranged on a straight line.

Figure 4:
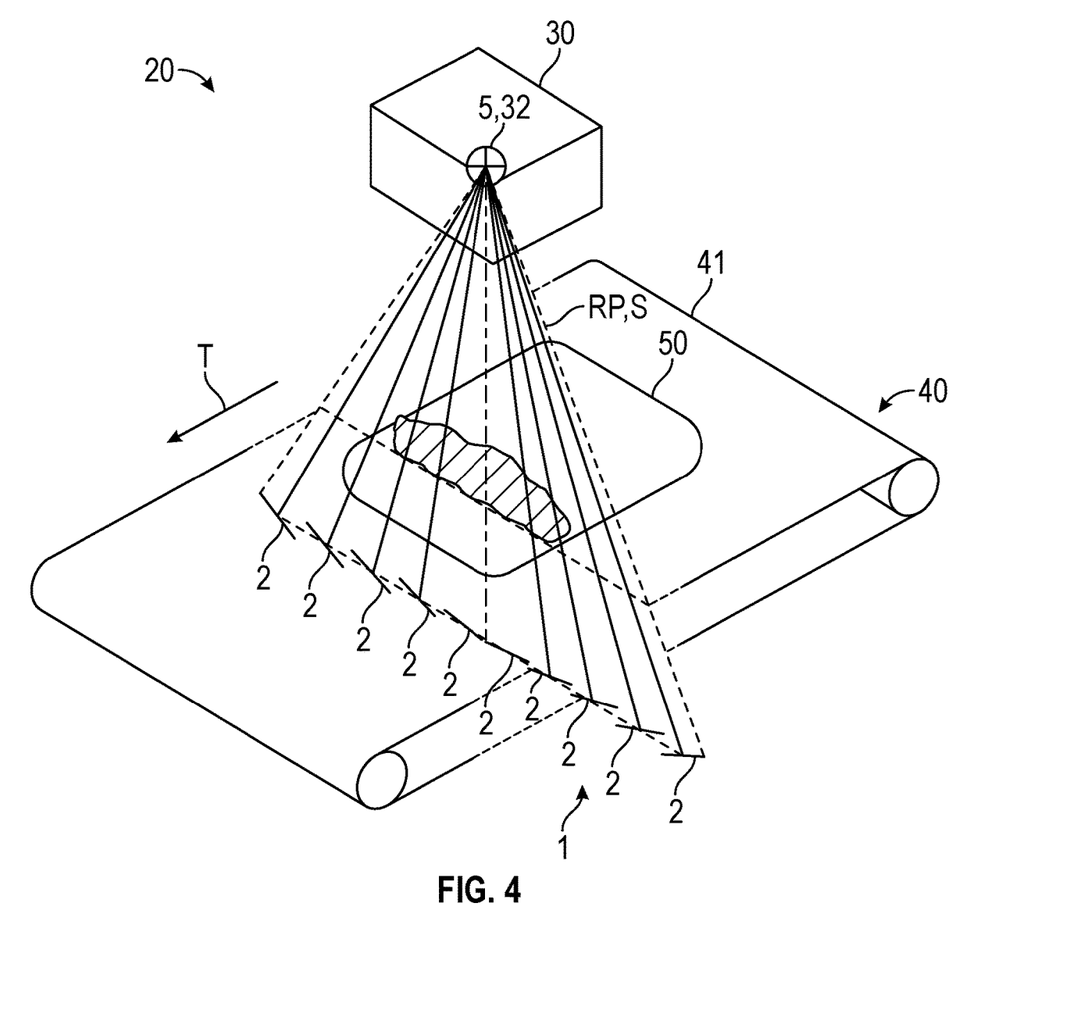
FIG. 4 is a perspective view of a radiographic inspection system according to the present invention.

FIG. 4 is a perspective view of a radiographic inspection system 20 according to the present invention. The radiographic inspection system 20 comprises a radiation source 30. The radiation source 30 may be an X-ray source. The radiation source produces a fan-shaped radiation beam 31, wherein the rays of said radiation beam span a radiation plane RP. The fan-shaped radiation beam 31 comprises a focal spot 32.

The radiographic inspection system 20 further comprises a detector array 1 according to the present invention. The detector array 1 may be the detector array 1 shown in FIGS. 1 and 2.

Furthermore, the radiographic inspection system 20 comprises transport means 40 for transporting an article 50 to be inspected along a transport direction T transversely, in particular perpendicularly, to said radiation plane RP. The transport means 40 comprises a conveyor belt 41 to transport the article 50 along the transport direction T. The article is transported in the inspection plane 8. The transport path T is interposed between the radiation source 30 and the detector array 1. The detector array 1 is arranged such that the common plane S coincides with the radiation plane RP. Furthermore, the common focus 5 of the detector array 1 mentioned above coincides with the focal spot 32 of the radiation source 30. The radiographic inspection system 20 shown in FIG. 4 is very compact, as the detector array 1 is very compact. Furthermore, the detector array 1 according to the present invention allows for high precision imaging of the article 50 to be inspected. The radiographic inspection system 20 may be used for X-ray absorption imaging.

What is claimed is:

1. An array for detecting electromagnetic radiation, comprising:
    a plurality of detector elements arranged consecutively along a scan line which extends in a first direction for receiving electromagnetic radiation and converting the received electromagnetic radiation into a detection signal;
    wherein each of said detector elements receive the electromagnetic radiation on a detection surface which has a plurality of surface normals, such that the surface normals of each of the detection surfaces extend in a common plane in the first direction and converge into a common focus;
    wherein the detector elements are arranged such that a distance from the common focus to at least two of the detection surfaces is different when each distance is measured along the surface normals of the respective at least two detection surfaces;
    wherein an end surface of each adjacent pair of said detector elements are provided in a facing relationship, are aligned along a straight line that passes through the common focus, and all centroids of the detection surfaces are aligned along a straight line.

2. The array of claim 1, wherein, for each of the detector elements, a neighboring detector element is positioned such that a distance from the common focus to the detection surface is different than a distance from the common focus to the detection surface of the neighboring detector element, when each measurement is made along the surface normal of the respective detection surfaces.

3. The array of claim 2, wherein, for each of the detection surfaces, the surface normal thereof that converges in the common focus passes through the centroid of the detection surface.

4. The detector array of claim 3, further comprising:
an inspection plane for arranging an article to be inspected, the inspection plane located between the common focus and at least one pair of the detector elements, such that:
a first of the detector elements has a surface normal through the centroid of the detection surface to the common focus that intersects the inspection plane at a point A;
a second of the detector elements has a surface normal through the centroid of the detection surface to the common focus that intersects the inspection plane at a point B;
along the respective surface normals, point A is at a distance a from the common focus and at a distance a' from the first detector element, and point B is at a distance b from the common focus and at a distance b' from the second detector element, wherein a ratio a/a' is equal to a ratio b/b'.

5. The array of claim 1, wherein at least one of the detection surfaces comprises a flat surface.

6. The array of claim 1, wherein at least one of the detection surfaces has a rectangular circumference.

7. The array of claim 1, wherein the detector elements are adapted to detect X-ray radiation.

8. The array of claim 7, wherein each of the detector elements comprises a scintillator.

9. The array of claim 1, wherein each of the detector elements comprises a stacked-type dual-energy electromagnetic radiation detection element that comprises a first detector member, adapted to detect radiation at a first energy level, and a second detector member, adapted to detect radiation at a second energy level that is higher than the first energy level, wherein the first detector member is positioned atop the second detector member to be closer to the common focus.

10. The array of claim 1, further comprising:
a support, on which each detector element is detachably mounted.

11. The array of claim 1, wherein, for each of the detection surfaces, the surface normal thereof that converges in the common focus passes through the centroid of the detection surface.

12. The array of claim 11, further comprising:
an inspection plane for arranging an article to be inspected, the inspection plane located between the common focus and at least one pair of the detector elements, such that:
a first of the detector elements has a surface normal through the centroid of the detection surface to the common focus that intersects the inspection plane at a point A;
a second of the detector elements has a surface normal through the centroid of the detection surface to the common focus that intersects the inspection plane at a point B;
along the respective surface normals, point A is at a distance a from the common focus and at a distance a' from the first detector element, and point B is at a distance b from the common focus and at a distance b' from the second detector element, wherein a ratio a/a' is equal to a ratio b/b'.

13. A system for radiographic inspection of an article to be inspected, comprising:
a radiation source for producing a radiation beam that comprises a bundle of rays spanning a radiation plane, the radiation beam comprising a focal spot;
an array for detecting electromagnetic radiation according to claim 1;
a transport means for transporting the article to be inspected along a transport path transverse to the radiation plane, the transport path being interposed between the radiation source and the array,
wherein the array is arranged such that the common plane of the array coincides with the radiation plane, and the common focus coincides with said focal spot.

14. The system of claim 13, wherein the transport means comprises a conveyor belt.

15. The system of claim 14, wherein the radiation source comprises an X-ray source.

16. The system of claim 13, wherein the radiation source comprises an X-ray source.

* * * * *

UNITED STATES PATENT AND TRADEMARK OFFICE
CERTIFICATE OF CORRECTION

| | |
|---|---|
| PATENT NO. | : 11,754,513 B2 |
| APPLICATION NO. | : 17/444322 |
| DATED | : September 12, 2023 |
| INVENTOR(S) | : Mahnke et al. |

It is certified that error appears in the above-identified patent and that said Letters Patent is hereby corrected as shown below:

In the Claims

In Column 11, Line 5, Claim 4, please delete "detector".

Signed and Sealed this
Fifth Day of December, 2023

Katherine Kelly Vidal
*Director of the United States Patent and Trademark Office*